US005597548A

United States Patent [19]
Sherry et al.

[11] Patent Number: 5,597,548
[45] Date of Patent: Jan. 28, 1997

[54] 13C ISOTOPOMER ANALYSES IN INTACT TISSUE USING (13C) HOMONUCLEAR DECOUPLING

[75] Inventors: A. Dean Sherry; Piyu Zhao; Craig R. Malloy, all of Dallas, Tex.

[73] Assignee: Board of Regents, The University of Texas System, Austin, Tex.

[21] Appl. No.: 497,779

[22] Filed: Jul. 3, 1995

Related U.S. Application Data

[63] Continuation of Ser. No. 220,102, Mar. 30, 1994, abandoned, which is a continuation-in-part of Ser. No. 555,270, Jul. 18, 1990, Pat. No. 5,413,917.

[51] Int. Cl.⁶ .............................. A61K 51/04; C12Q 1/00; C12Q 1/02; C12Q 1/04
[52] U.S. Cl. .................................. 424/9.3; 435/35; 435/4; 435/14; 435/29; 435/30; 436/59; 436/57; 436/63; 436/173; 424/9.35; 424/1.81; 128/653.4; 128/654
[58] Field of Search .................................. 435/4, 35, 14, 435/30, 29; 436/173, 57, 56, 63; 424/9, 9.35, 1.11, 9.0, 1.17, 1.81, 9.3, 1.21; 324/300, 307, 311, 316; 128/653.4, 654

[56] References Cited

PUBLICATIONS

Avison et al., "Detection of Human Muscle Glycogen by Natural Abundance $^{13}$C NMR," *Proc. Natl. Acad. Sci. USA*, 85:1634–1636, Mar. 1988.

Behar et al., "Detection of Metabolites in Rabbit Brain by $^{13}$C NMR Spectroscopy following Administration if [1–$^{13}$C] Glucose," *Magnetic Resonance in Medicine*, 3:911–920, 1986.

Bottomley et al., "Proton–Decoupled, Overhauser–Enhanced, Spatially Localized Carbon–13 Spectroscopy in Humans," *Magnetic Resonance in Medicine*, 12:348–363, 1989.

Brown et al., "Delineation of Myocardial Oxygen Utilization With Carbon–11–Labeled Acetate," *Circulation*, 76(3):687–696, 1987.

Chance et al., "Mathematical Analysis of Isotope Labeling in the Citric Acid Cycle with Applications to $^{13}$C NMR Studies in Perfused Rat Hearts," *The J. of Biolog. Chem.*, 258(2):13785–13794, 1983.

Chatzidakis and Otto, "Labeled Oxidation Produces from [1–$^{14}$C], [U–$^{14}$C] and [16–$^{14}$C] Palmitate in Hepatocytes and Mitochondria," *Lipids*, 22(9):620–627, (1987).

Cohen, "Simultaneous $^{13}$C and $^{31}$P NMR Studies of Perfused Rat Liver," *The J. of Biolog. Chem.*, 258 (23):14292–14308, 1983.

Heerschap et al., "Broadband Proton Decoupled Natural Abundance $^{13}$C NMR Spectroscopy of Humans at 1.5 T", (1989).

Jue et al., "Natural Abundance $^{13}$C NMR Spectrum of Glycogen in Humans," *Magnetic Resonance in Medicine*, 5:377–379, 1987.

Keifo and Peuhkurinen, "Regulation of the Tricarboxylic Acid Cycle Pool Size in Heart Muscle," *J. Mol. Cell. Cardiol.*, 16:487–495, 1984.

Kornberg, "Anaplerotic Sequences and their Role in Metabolism," *Essays in Biochem.*, 2:1–31, 1966.

Le Cocq and Lallemand, "Precise Carbon–13 N.M.R. Multiplicity Determination," *J.C.S. Chem. Comm.*, 150–152, 1981.

Lerch et al., "Localization of Viable, Ischemic Myocardium by Positron–emission Tomography with $^{11}$C–Palmitate," *Circulation*, 64(4):689–699, 1981.

Liedtke et al., "Changes in Substrate Metabolism and Effects of Excess Fatty Acids in Reperfused Myocardium," *Circulation Research*, 62(3):535–542, Mar. 1988.

London, "$^{13}$C Labeling in Metabolic Regulation Studies," *Prog. in NMR Spectroscopy*, 20:337–383, 1988.

Magnusson et al., "Increased Rate of Gluconeogenesis in Type II Diabetes Mellitus; A $^{13}$C Nuclear Magnetic Resonance Study," *J. Clin. Invest.*, 90:1323–1327, Oct. 1992.

Malloy, "Analysis of Substrate Utilization by $^{13}$C NMR Spectroscopy," *Structural and Organizational Aspects of Metabolic Regulation*, 363–374, 1990.

Malloy et al., "Contribution of Exogenous Substrates to Acetyl Coenzyme A: Measurements by 13C NMR Under Non–Steady–State Conditions," *Biochemistry*, 29(29):6756–6761, (1990).

Malloy et al., "Evaluation of Carbon Flux and Substrate Selection Through Alternative Pathways Involving the Citric Acid Cycle of the Heart by $^{13}$C NMR Spectroscopy," *J. of Biolog. Chem.*, 263(15):6964–6971, 1988.

Mickle et al., "Exogenous Substrate Preference of the Post–Ischaemic Myocardium," *Cardiovascular Research*, 20:256–263, 1986.

(List continued on next page.)

*Primary Examiner*—Gary E. Hollinden
*Assistant Examiner*—Micheal G. Hartley
*Attorney, Agent, or Firm*—Arnold, White & Durkee

[57] ABSTRACT

Entry of $^{13}$C–enriched acetyl-CoA into the citric acid cycle results in scrambling of $^{13}$C into the various carbon positions of all intermediate pools. The eventual result is that the $^{13}$C resonances of all detectable intermediates or molecules exchanging with those intermediates appear as multiplets due to nearest neighbor spin-spin couplings. Isotopomer analysis of the glutamate $^{13}$C multiplets provides a history of $^{13}$C flow through the cycle pools. Relative substrate utilization and relative anaplerotic flux can be quantitated. A major limitation of the method for in vivo applications is spectral resolution of multi-line resonances required for a complete isotopomer analysis. It is now shown that ($^{13}$C)homonuclear decoupling of the glutamate C3 resonance collapses nine-line C4 and C2 resonances into three line multiplets. These three-line $^{13}$C multiplets are well resolved in isolated, perfused rat hearts and present steady-state equations which allow an isotopomer analysis from data obtained in intact tissue. This advancement shows for the first time that $^{13}$C isotopomer methods may be extended to complex metabolic conditions for resolution of carbon-carbon coupling, and particularly to in vivo measurements.

12 Claims, 7 Drawing Sheets

PUBLICATIONS

Moreland and Carroll, "$^{13}C-^{13}C$ Dipolar Interactions as a Relaxation Mechanism," *J. of Magnetic Resonance*, 15:596–599, 1974.

Myears et al., "Substrate Use in Ischemic and Reperfused Canine Myocardium: Quantitative Considerations," *American Physiological Society*, H107–H114, 1987.

Neely et al., "The Effects of Increased Heart Work on the Tricarboxylate Cycle and its Interactions with Glycolysis in the Perfused Rat Heart," *Biochem. J.*, 128:147–159, 1972.

Patt and Shoolery, "Attached Proton Test for Carbon–13 NMR," *J. of Magnetic Resonance*, 46:535–539, 1982.

Rothman et al., "Quantitation of Hepatic Glycogenolysis and Gluconeogenesis in Fasting Humans with $^{13}C$ NMR," *Science*, 254:573–576, Oct. 1991.

Schwaiger et al., "Retention and Clearance of C–11 Palmitic Acid in Ischemic and Reperfused Canine Myocardium," *JACC*, 6(2):311–320, Aug. 1985.

Sherry et al., "Alterations in Substrate Utilization in the Reperfused Myocardium: A Direct Analysis by $^{13}C$ NMR," *Biochemistry*, 31:4833–4837, 1992.

Sherry et al., "Propionate Metabolism in the Rat Heart By $^{13}C$ n.m.r. Spectroscopy," *Biochem. J.*, 254:529–598, 1988.

Shulman et al., "Quantitation of Muscle Glycogen Synthesis in Normal Subjects and Subjects with Non–Insulin–Dependent Diabetes by $^{13}C$ Nuclear Magnetic Resonance Spectroscopy," *The New England Journal of Medicine*, 322(4):223–228, Jan. 1990.

Veerkamp et al., "$^{14}CO_2$ Production Is No Adequate Measure of [$^{14}C$] Fatty Acid Oxidation," *Biochemical Medicine and Metabolic Biology*, 35:248–259, 1986.

Walker and London, "Biosynthetic Preparation of L–[$^{13}C$]– and [$^{15}N$] Glutamate by *Brevibacterium flavum*," *Applied and Environmental Microbiology*, 53(1):92–98, 1987.

Walker et al., "$^{13}C$ Nuclear Magnetic Resonance Studies of the Biosynthesis by *Microbacterium ammoniaphilum* of L–Glutamate Selectively Enriched with Carbon–13," *The Journal of Biological Chemistry*, 257(3):1189–1195, 1982.

Walsh and Koshland, "Determination of Flux Through the Branch Point of Two Metabolic Cycles; The Tricarboxylic Acid Cycle and the Glyoxylate Shunt," *The Journal of Biological Chemistry*, 259(15):9646–9654, Aug. 1984.

Weiss et al., "Indexing Tricarboxylic Acid Cycle Flux in Intact Hearts by Carbon–13 Nuclear Magnetic Resonance," *Circulation Research*, 70(2), Feb. 1992.

Weiss et al., "Tricarboxylic Acid Cycle Activity in Postischemic Rat Hearts," *Circulation*, 87(1), Jan. 1993.

Williamson, "Effects of Insulin and Diet on the Metabolism of L(+)– Lactate and Glucose by the Perfused Rat Heart," *J. Biochem.*, 83:377–383, 1962.

Williamson and Krebs, "Acetoacetate as Fuel of Respiration in the Perfused Rat Heart," *Biochem. J.*, 80:540–547, 1961.

Wyns et al., "Effects of Inhibition of Fatty Acid Oxidation on Myocardial Kinetics of $^{11}C$–Labeled Palmitate," *Circulation research*, 65(6):1787–1797, 1989.

Malloy et al., "Carbon flux through citric acid cycle pathways in perfused heart by $^{13}C$ NMR spectroscopy," *Febs Letters*, 212(1):58–62, 1987.

Cohen, "Effects of Insulin Perfused Liver from Streptozotocin–Diabetic and Untreated Rates: Assay of Pyruvate Kinase Flux," *Biochemistry*, 26(2):573–580, 1987.

Cohen, "$^{13}C$ NMR Study of Fasting and Diabetes on the Metabolism of Pyruvate in the Tricarboxylic Acid Cycle and of the Utilization of Pyruvate and Ethanol in Lipogenesis in Perfused Rat Liver," *Biochemistry*, 26(2):581–589, 1987.

International Search Report dated Jan. 17, 1992.

Sherry et al., "Metabolic Studies of Pyruvate and Lactate–Perfused Guinea Pig Hearts By 13C NMR," *Journal of Biological Chemistry*, 260(16):9272–9279, 1985.

Bader–Goffer et al., "Cerebral Metabolism of Acetate and Glucose Studied by 13C–NMR Spectroscopy," *The Biochemical Journal*, 266(1):133–139, 1990.

Malloy et al., "Contribution of Exogenous Substrates to Acetyl Coenzyme A: Measurements by 13C NMR Under Non–Steady–State Conditions," *Biochemistry*, 29(29):6756–6761, (1990).

Beckmann et al., "$^{13}C$ NMR for the Assessment of Human Brain Glucose Metabolism in Vivo," *Biochemistry*, 30:6362–6366, 1991.

Beckmann et al., "$^{13}C$ MRS of the Human Grain Infusion of [1–$^{13}C$] Glucose," *Society of Magnetic Resonance in Medicine Book Abstracts*, p. 3320, 1992.

Beckmann, "In Vivo $^{13}C$ Spectroscopy in Humans," *NMR: Basic Principles and Progress Editors: P. Diehl, E. Fluck, H. Gunther, R. Kosfeld, J. Seelig, Springer Verlag*, pp. 73–100, 1992.

Behar et al., "Detection of Metabolites in Rabbit Brain by $^{13}C$ NMR Spectroscopy following Administration if [1–$^{13}C$] Glucose," *Magnetic Resonance in Medicine*, 3:911–920, 1986.

Cerdan et al., "Cerebral Metabolism of [1, 2–$^{13}C_2$]Acetate as Detected by in Vivo and in Vitro $^{13}C$ NMR," *The Journal of Biological Chemistry*, 265(22):12916–12926, 1990.

Evans et al., "[$^{13}C$]Propionate oxidation in wild–type and citrate synthase mutant *Escherichia coli*: evidence for multiple pathways of propionate utilization," *Biochem. J.*, 291:927–932, 1993.

Gruetter et al., "Localized $^{13}C$ NMR of Amino Acids in the Human Brain in Vivo," *Society of Magnetic Resonance in Medicine Book of Abstracts*, p. 1921, 1992.

Lavanchy et al., "Glycogen metabolism: a $^{13}C$–NMR study on the isolatied perfused rat heart," *Febs*, 178(1):34–38, 1984.

Neurohr et al., "Carbon–13 Nuclear Magnetic Resonance Studies of Myocardial Glycogen Metabolism in Live Guinea Pigs," *Biochemistry*, 23:5029–5035, 1984.

Rothman et al., "$^1H$ –Observe/$^{13}C$–decouple spectroscopic measurements of lactate and glutamate in the rat brain in vitro," *Proc. Natl. Acad. Sci. USA*, 82:1633–1637, 1985.

Seeholzer, "$^{13}C$ Nuclear Magnetic Resonance Studies of Cardiac Metabolism," *Dissertation Abtracts International*, 46(11):3683–B, 1986.

$^{13}$C ISOTOPOMER ANALYSES IN INTACT TISSUE USING ($^{13}$C) HOMONUCLEAR DECOUPLING

The United States Government has certain rights in the present invention pursuant to the terms of Grant No. HL 34557 awarded by the National Institutes of Health and a Merit Review and Career Development award from the Department of Veteran's Affairs.

This application is a continuation of application Ser. No. 08/220,102, filed Mar. 30, 1994, now abandoned, which is a continuation-in-part application of U.S. patent application Ser. No. 07\555,270 filed Jul. 18, 1990, U.S. Pat. No. 5,413,917, the entire text of which is herein incorporated by reference and without disclaimer.

BACKGROUND OF THE INVENTION

1. Field of the Invention

The present invention is concerned with methods of determining substrate utilization in living tissue. More particularly, the methods employ NMR isotopomer analysis of $^{13}$C-labeled substrate spectra obtained from the tissue, allowing a rapid, single measurement under nonsteady state conditions of substrate utilization which may be used to assess tissue damage. The analysis utilizes a homonuclear decoupling method of spectrum simplification providing collapse of a multiplet to allow precise determination of peak areas.

2. Description of Related Art

The relative rates of utilization of various exogenous and/or endogenous substrates in normal cells and tissues may be sensitive to many factors including cellular work rate, physiologic state, drugs, toxins, hormones, and the like. Substrate utilization may also be sensitive to disease states such as ischemia, infection, inflammation, trauma, congenital defects in metabolism, acquired defects in metabolism, or during malignant transformations such as cancer. Thus, precise quantitation of substrate utilization could have broad application since it may provide insight into the integrated functional state and viability of cells or a tissue.

Acetyl Coenzyme A (acetyl-CoA) is a key intermediate in cellular biochemistry. It is oxidized in the citric acid cycle for the production of energy, and it is a precursor in multiple biosynthetic processes. Acetyl-CoA may be derived frown numerous compounds, each of which must be metabolized through different pathways subject to complex and interacting regulatory processes. Thus, the relative contribution of one or more substrates to acetyl-CoA reflects cellular metabolic state. Since this measurement is so important for the understanding of tissue metabolism, it has been the objective of numerous studies in many cellular preparations and tissues, particularly heart tissue (more recent citations include, for example, Jue, et al., 1987; Avison, et al., 1988; Bottomley, et al., 1989; Heershap, et al., 1990; Shuhnan, et al., 1990; Rothman, et al., 1991; and Magnusson, et al., 1992).

The measurement of the contribution of a compound to acetyl-CoA ordinarily requires an estimate of the rate of acetyl-CoA utilization, typically from oxygen consumption, and the rate of substrate utilization under steady-state conditions. The latter usually is measured by the rate of appearance of $^{14}CO_2$ from a $^{14}$C-enriched substrate, the rate of removal of substrate from the perfusion medium, or multi-exponential analysis of $^{11}$C time-activity curves in tissues utilizing $^{11}$C-enriched substrates.

However, substrate and oxygen removal are difficult to measure under some important conditions, and metabolic and isotopic steady-state often cannot be assured. Further, since pyruvate may be metabolized by either pyruvate dehydrogenase or through a pyruvate carboxylation pathway, the appearance of $^{14}CO_2$ from $^{14}$C-enriched pyruvate (or its precursors) indicates net substrate oxidation only if the carbon skeleton enters the citric acid cycle via pyruvate dehydrogenase. Similarly, $^{14}CO_2$ release from fatty acids is an unreliable measure of this oxidation (Chatzidakis and Otto, 1987; Veerkamp, et al., 1986). Thus, standard methods for assessing substrate competition and oxidation are often not satisfactory for rapidly changing or spatially heterogeneous metabolic states, or if more than one pathway is available for carbon flow into the citric acid cycle.

In spite of these limitations on traditional methods, there is substantial interest in the measurement of substrate oxidation for the assessment of tissue metabolism and viability. For example, position emission tomography (PET) has been used to examine regional myocardial metabolism during ischemic and other states. However, the interpretation of some PET observations is controversial, for example, fatty acid oxidation in ischemic reperfused myocardium. PET studies generally have concluded that fatty acid oxidation is suppressed, but other reports have not validated this finding (Mickel, et al., 1986; Myears, et al., 1987: Liedke, et al., 1988; Wyns, et al., 1989: Lerch, et al., 1981; Schwaiger, et al., 1985). PET is fundamentally limited by the lack of knowledge of the chemical state of the tracer. For example, a compound may enter a cell where it may be trapped and stored, metabolized to acetyl-CoA and oxidized, or it may remain in the cell briefly and then diffuse out, unchanged. Numerous assumptions regarding the metabolic fate of a tracer are therefore required.

For these reasons, some recent PET studies have emphasized the utilization of a very simple compound, acetate, which is not subject to many of the complex physiological processes which regulate normal metabolism (Brown, et al., 1987). Analysis of the results is thereby simplified, but acetate is not a physiological substrate. Biochemical and physiological studies using $^{11}$C are also limited by the problem of working with a radioactive element with a very short half-life. Thus, a nearby cyclotron is essential, and rapid chemical synthesis is required. The study of some molecules or certain labeling patterns is simply not practical.

The analogous use of $^{13}$C enriched substrates to monitor intermediary metabolism has been established (London, 1988). Multiple enriched intermediates of the citric acid cycle may be detected by NMR spectroscopy (London, 1988; Walker, et al., 1982; Chance, et al., 1983: Cohen, 1983; Walker and London, 1987; Malloy, et al., 1990A). It has been shown that citric acid cycle flux may be determined if the fractional enrichments in intermediates are measured repeatedly after the addition of enriched substrate (Chance, et al., 1983). This method, however, assumes steady-state flux conditions, constant intermediate pool sizes, and good temporal resolution. Although collection of in vivo data is theoretically possible, the method depends on measurement of fractional enrichment in glutamate and other intermediates, a requirement which may be difficult to meet under many important conditions.

An alternative to the measurement of absolute citric acid cycle flux is the measurement of the relative rates of competing pathways feeding acetyl-CoA. This approach has been reported previously. In some instances, metabolic and isotopic steady-state were assumed for the purposes of data analysis and these conditions were established experimentally (Malloy, et al., 1988, 1990A; Sherry, et al., 1988). Other reports indicated that insight into the pathways feeding acetyl-CoA could be obtained by $^{13}$C NMR spectroscopy (Cohen, 1983; Walker and London, 1987). Finally, recent reports describe how to measure the ratio of the contribution of two labeled substrates to acetyl-CoA under nonsteady-state conditions (Malloy, 1990B, 1990C; Sherry, et al., 1992). Up to three labeled substances can be analyzed and the fraction of unlabeled acetyl CoA can be determined by a non steady state analysis (Malloy, et al., 1990B).

$^{13}$C NMR is useful for the monitoring of metabolism of $^{13}$C labeled compounds in experimental animals and humans. However, there are three important factors limiting study of substrate utilization in vivo. First, there is the consideration of expense. Significant amounts of relatively expensive labeled compounds make it difficult to maintain a constant concentration in the blood for the time required to attain isotopic steady-state. Second, many conditions of interest may involve rapidly changing metabolic conditions, and metabolic state cannot be assumed. Finally, an isotopomer analysis applicable in vivo to determine $^{13}$C contributions to the carbon skeleton of citric acid cycle components has been applied only when $B_0$ homogeneity was sufficient to allow resolution of $^{13}$C-$^{13}$C scalar coupling. This condition of homogeneity does not occur under the circumstances of many in vivo measurements.

$^{13}$C in labeled compounds can be detected in humans. The most widely examined pathways in humans to date have been those involving either storage of glucose or mobilization of glycogen. The C 1 resonance of glycogen has been detected by numerous groups in both human liver and muscle. The rate of net hepatic glycogenolysis in fasted humans has been determined by monitoring the time dependent signal of natural abundance glycogen. This in combination with glucose production rates measured by turnover of [6-$^3$H]glucose, has allowed an estimate of gluconeogenic rates in normal controls and in patients with type II diabetes mellitus. [1-$^{13}$C]glucose levels in human brain have also been quantitated to yield an estimate of glucose transport rates. Some metabolic end-products of [1-$^{13}$C]glucose have also been detected in human brain and incorporation of $^{13}$C into [4-$^{13}$C]glutamate has been used to estimate citric acid cycle flux.

Thus $^{13}$C from labeled isotopes can be detected in vivo and isotopomer methods provide substantial information. Although the isotopomer method would be of most practical value for in vivo applications, it has until now not yet been successfully applied, largely because of difficulties in resolving those multiplets in spectra obtained from intact tissue. There is thus a need to develop methods for quantitative substrate selection in intact tissue in the whole, live animal. This would be of particular benefit in recent heart attack patients to determine damaging effects of ischemia. Similarly, analyses of tissue damage for stroke and brain injured patients could be obtained rapidly and efficiently with a single measurement.

SUMMARY OF THE INVENTION

The present invention addresses the foregoing and other problems by providing means of determining substrate utilization in actively metabolizing tissues, and in particular as showing that [$^{13}$C]homonuclear decoupling may be employed to simplify in vivo $^{13}$C spectra. The inventors have illustrated the method with spectra of [$^{13}$C]homonuclear decoupled perfused rat hearts by quantitation of substrate selection in intact tissue. Specifically, the inventors have shown that homonuclear decoupling methods resolve $^{13}$C NMR multiplets obtained from perfused, beating hearts. The method is applicable for analysis of substrate oxidation in the liver which may be sensitive to numerous disorders and the effects of xenobiotics.

The present invention has also addressed the problem of nonsteady-state conditions and field homogeneity requirements. It is shown that the contribution of one or more exogenously administered $^{13}$C-labeled substrates to acetyl CoA can be determined in a tissue or cell using $^{13}$C NMR without the constraint of metabolic or isotopic steady-state. With the development of homonuclear decoupling applied to $^{13}$C spectra, the method permits such determinations of substrate utilization even when spectral lines are broad due to $B_0$ inhomogeneity, an important advancement which has paved the way for substrate utilization studies in vivo. The method does not require many of the simplifying assumptions involved in $^{11}$C or $^{14}$C methods, and, since a stable isotope, $^{13}$C, is used, a wide variety of compounds with complex labeling patterns may be synthesized and studied.

The inventors have solved two major problems that arise in attempting to make measurements relating to substrate utilization, First, it has been discovered that one may administer $^{13}$C labeled substrates and then measure a single spectrum before steady-state metabolic or isotopic steady-state has been achieved. For in vitro determinations, the measurement need be made only on a single tissue sample so that in human patients there is decreased stress from not having to obtain multiple tissue samples. Measurement is made shortly after the administration of labeled substrate, eliminating need for infusion or perfusion of large quantities of substrate. This may make a significant difference in cost.

Secondly, the inventors have shown that a homonuclear decoupling method may be employed in cases where a single $^{13}$C NMR spectrum is insufficiently resolved to obtain accurate data to determine substrate utilization. This is frequently encountered in in vivo determinations, as for example where the particular $^{13}$C multiplet peaks required for analysis are unresolved and therefore do not allow determination of critical ratios. The inventors found this a consistent problem in spectra obtained from perfused, beating hearts. The problem was solved by using the homonuclear decoupling methods disclosed herein.

Figure 4A:
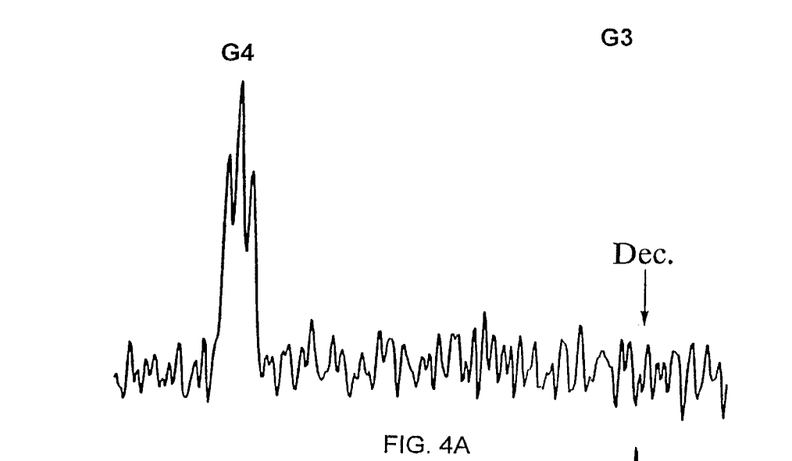
FIG. 4A is a normal spectrum.
Figure 4B:
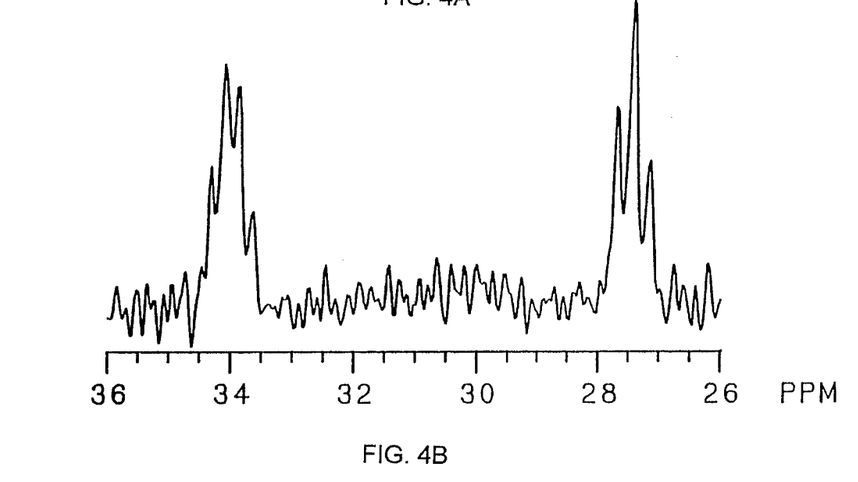
Figure 5A:
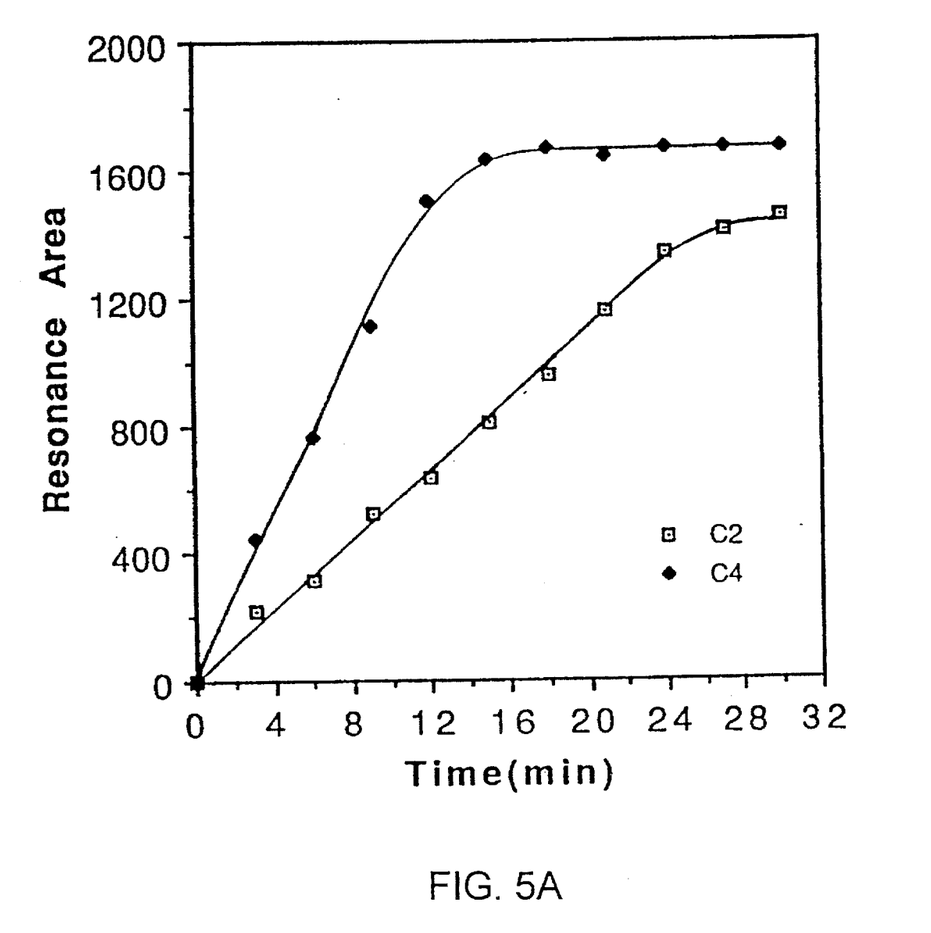
FIG. 5A shows continuous homonuclear decoupling of glutamate C3.

Proceeding from the discovery that accurate substrate utilization may be obtained from a single NMR measurement under nonsteady state conditions, the inventors have shown that [$^{13}$C]homonuclear decoupling simplifies the $^{13}$C MRS spectrum of intact hearts utilizing mixtures of $^{13}$C enriched substrates without significant loss of the metabolic information contained within the glutamate $^{13}$C multiplet resonances. Decoupling of glutamate C3 collapses the normally nine-line glutamate C2 and C4 multiplets into three lines, with a separation of 52 Hz between the outer resonances. The resulting singlet and doublet resonances is well enough resolved in intact, perfused rat hearts to allow quantitation of their relative areas (FIGS. 4B and 5A). This offers for the first time the opportunity of performing a $^{13}$C isotopomer analysis in vivo.

The inventors have developed steady-state equations which relate the areas of C2S' and C4S' and the total C4/C2 area ratio in a [C3]homonuclear decoupled spectrum of glutamate to the fractional enrichment levels of singly ($F_{c2}$) and doubly ($F_{c3}$) enriched acetyl-CoA entering the citric acid cycle plus y, the ratio of anaplerotic to citric acid cycle flux. These parameters agree well with results obtained from a complete steady-state analysis of extract spectra. The C4S'/C4D' ratio directly reports relative substrate utilization and is not affected by changing pool sizes, anaplerosis, or nonsteady-state metabolic or isotopic conditions. This makes the method extremely attractive for in vivo applications where steady-state conditions cannot always be assured. Another obvious advantage of the method is that [$^{13}$C]homonuclear decoupling of glutamate C3 increases the signal-to-noise in the C2 and C4 resonances (see FIGS. 1B, 3A and 4A) thereby allowing excellent temporal resolution of data such as that shown in FIG. 5A.

Measurements are conveniently made using nuclear magnetic resonance. This is a powerful technique and at present is the method of choice for determining isotope distribution. $^{13}$C NMR measurements are typically performed by determining total resonance areas attributed to the different carbon atoms of the molecules selected for measurements and the multiplets within each resonance. Appropriate corrections for nuclear Overhauser effects and $^{13}$C-$^{13}$C interactions which affect $T_1$ may be required. The method is not limited to the administration of a single $^{13}$C-labeled substrate; in fact, the inventors have administered up to three $^{13}$C-labeled compounds. To determine utilization of a single $^{13}$C-labeled compound, resonance areas of a multiplet of carbon C4 and a resonance area ratio of carbons C4 and C3. For two $^{13}$C-labeled substrates, the $^{13}$C NMR resonance areas of two multiplets of carbon C4 and resonance area ratios of carbon C3 to C4 are measured. Under some conditions the ratio of C5 to C4 must be measured. Substrate utilization for three administered $^{13}$C-labeled compounds involves measuring $^{13}$C NMR resonance areas of two multiplets of carbon C4 and a resonance area ratios of carbon C3 to C4 and C5 to C4.

Position of $^{13}$C-labeling in the administered compound determines the position of the $^{13}$C in the skeleton of the compound which is a component of the citric acid cycle. All compounds entering the citric acid cycle through acetyl-CoA will show labels in the skeletal 3 and 4 positions of components of the citric acid cycle when the acetyl-CoA is labeled in the number 2 position of the acetate group. If the acetyl carbon 1 position is labeled with $^{13}$C, an enrichment in the C5 position of the skeletal components of the citric acid cycle will be observed. When the carbon C5 position is enriched, $^{13}$C NMR measurements will include measuring multiplets in the $^{13}$C NMR resonance of the C5 carbon. As discussed, it may be necessary to make corrections for the effects of $^{13}$C-$^{13}$C dipolar interactions on $T_1$ and nuclear Overhauser effects under these conditions.

The methods of the present invention allow one to rapidly and conveniently obtain substrate utilization, either in tissue samples or directly in vivo. As typically practiced, the invention involves using at least one labeled carbon compound having carbons which are capable of entering the citric acid cycle, administering the compound in vitro or in vivo to cells or a tissue having citric acid cycle capacity, and then measuring the enrichment pattern in a citric acid cycle component or in the carbons of a compound that exchange with the citric acid cycle. A particular advantage is that measurements are made prior to achievement of steady-state isotopic carbon distribution; consequently, measurements may often be made as early as a few minutes after a labeled substrate is supplied to the cell or tissue. For in vivo measurements, some labeled compounds may require administration over longer periods, e.g., 30 min or so, after which a spectrum may be taken.

After the labeled compound has been administered, the enrichment pattern in one or more products is measured. The measurement is performed on a compound within the citric acid cycle or on a compound that can exchange carbon atoms into the citric acid cycle. The compound which is used for the determination of labeling patterns must preserve the distribution of carbon label in C3, C4 and C5 of α-ketoglutarate. In many cases, the most convenient compound for making labeled carbon measurements is glutamate. Glutamate is in rapid equilibrium with α-ketoglutarate of citric acid cycle. However, in practice, any equivalent component of the citric acid could be used, including derivatives of citrate, isocitrate, cis-aconitate, α-ketoglutarate, glutamine, γ-aminobutyric acid and the like.

The $^{13}$C labeling pattern in the substrate is selected by the operator after considering the labeling pattern in acetyl CoA after the substrate is metabolized through known biochemical pathways. Table 1 illustrates the flexibility of the method and shows the expected labeling pattern in acetyl CoA depending on the number of substrates to be investigated.

| Number of Labeled /Substrates | Labeling Pattern in Acetyl-CoA | Example of Labeled Substrate |
|---|---|---|
| 1 | [2-$^{13}$C] acetyl-CoA or [1,2-$^{13}$C] acetyl-CoA | [3-$^{13}$C] pyruvate or [2,3-$^{13}$C] pyruvate |
| 2 | [2-$^{13}$C] acetyl-CoA and [1,2-$^{13}$C] acetyl-CoA or [1,2-$^{13}$C] acetyl-CoA and [1-$^{13}$C] acetyl-CoA or [2-$^{13}$C] acetyl-CoA and [1-$^{13}$C] acetyl-CoA | [3-$^{13}$C] pyruvate and [U-$^{13}$C] glucose [2,3-$^{13}$C] pyruvate and [1-$^{13}$C] acetate [3-$^{13}$C] pyruvate and [1-$^{13}$C] acetate |
| 3 | [1-$^{13}$C] acetyl-CoA and [1,2-$^{13}$C] acetyl-CoA and [2-$^{13}$C] acetyl-CoA | [2-$^{13}$C] pyruvate and [U-$^{13}$C] fatty acid and [1-$^{13}$C] glucose |

Examples of suitable substrates include acetate, lactate, pyruvate, glucose and other sugars, alanine and other amino acids, ethanol, acetoacetate and other ketone bodies, and short, medium or long chain fatty acids. Alternatively, the labeled carbon may enter the citric acid cycle through intermediates other than acetyl CoA such as the case of propionate oxidation, an anaplerotic reaction (Kornberg, 1966; Sherry, et al., 1988). However, it is essential that the labeled carbon eventually reach acetyl-CoA in order that the C4 and/or C5 of citrate become enriched. A third group of labeled compounds may already be members of the citric acid cycle such as citrate, isocitrate, cis-aconitate or α-ketoglutarate. In this case the method enables the effective contribution of that compound to acetyl-CoA.

There are numerous examples of applications of the disclosed methods, in both in vitro and in vivo measurements. Measurements of substrate utilization in the heart and brain are of particular importance in view of the prevalence of heart disease and stroke in modern populations.

Assessment of brain metabolic state will likely most conveniently be done by administering $^{13}$C-labeled glucose would to the brain. This could be done in a variety of ways, including appropriate administration of the $^{13}$C-labeled glucose as by intravenous injection. A $^{13}$C NMR measurement would be performed on the brain after the tissue had been exposed to the $^{13}$C-labeled glucose. The time of exposure naturally would depend on the nature of the determination and conditions, but would generally be performed shortly after administering the $^{13}$C-labeled glucose. It is one of the unique aspects of this invention that measurement may be made before metabolic or isotopic steady-state is attained.

Another important use of this method is the in vivo determination of regional variations in substrate utilization of ischemic tissue. This involves the steps of administering a $^{13}$C-labeled compound and then performing a $^{13}$C NMR measurement on the tissue sample after the tissue has been exposed to the compound. As discussed, the measurement may be performed before metabolic and isotopomeric steady-state has been achieved. Regional substrate utilization can be determined, a method which would be particularly useful in determining tissue damage after heart attacks in experimental animals or human patients.

Many other applications using the method of the present invention are envisioned. These include metabolism studies in biopsied tissue, integration with NMR imaging methods, imaging substrate utilization, analysis of consequences of genetic engineering and cellular identification through metabolic fingerprinting.

In determining metabolism in biopsied tissues, one to three $^{13}$C-enriched substrates may be infused into an animal or human for diagnostic purposes. The tissue of interest such as an abnormal mass could be biopsied surgically using standard procedures, or studied directly in vivo by NMR measurement taken on a subject placed in the NMR spectrometer. The biopsied sample is then extracted using standard methods, studied by NMR or other techniques and analyzed using the described method.

Construction of images based on spatially resolved spectroscopic data is also well known to those skilled in the art. For example, current methods allow the acquisition of $^{31}$P NMR spectra from multiple volumes in the human brain, heart and other organs. These spectra may be presented as images of information selectively derived from the $^{31}$P NMR spectrum, such as an image of phosphocreatine concentration. In a similar manner, the acquisition of the spectra described herein and application of the analysis would allow construction of quantitative images of substrate utilization in animals and humans.

The genome of a cell line or tissue may be modified using current methods of genetic engineering. These modifications may have specific and anticipated consequences (for example, reduced activity of an enzyme) or extensive and unexpected consequences for intermediary metabolism. This method would provide a very simple and convenient technique to prove that the expected effects of genetic engineering have occurred, to investigate the overall consequences for cellular metabolism, or to look for unanticipated consequences of the intervention.

Metabolic fingerprinting is yet another variation of the present invention. Cell lines or cultures of prokaryotes such as bacteria or eukaryotes such as yeast or tumor cells have variable requirements for exogenous substrate. The patterns of substrate utilization when multiple substrates are available may be characteristic of a particular cell line. One may provide one to three labeled compounds to the cells. The compounds should be judiciously selected to probe specific pathways; for example, transamination, activity of pyruvate dehydrogenase, activity of beta oxidation, activity of glycolysis and similar activities. NMR obtained in vivo or from tissue extracts is then subjected to the analysis of the present invention.

BRIEF DESCRIPTION OF THE DRAWINGS

FIG. 1A is a normal $^{13}$C spectrum. FIG. 1B is a [C3]homonuclear decoupled $^{13}$C spectrum. The scheme at the right in each of FIGS. 1A and 1B illustrates that C4S+C4D34 in the coupled spectrum collapse to C4S' while C4D45+C4Q collapse to C4D' upon homonuclear decoupling of glutamate C3.

FIGS. 3A and 3B show a $^{13}$C MRS spectra of an intact rat heart perfused with 3 mM [1,2-$^{13}$C]acetate.

FIGS. 4A and 4B are $^{13}$C MRS spectra of the same heart as shown in FIG. 2 after adding an additional ~1.5 mM [2-$^{13}$C]acetate to the perfusate. FIG. 4B is a C3 homonuclear decoupled spectrum. Note that the singlet/doublet ratio (C4S'/C4D') in the glutamate C4 resonance in the decoupled spectrum (top) directly reports the relative utilization of [2-$^{13}$C]acetate versus [1,2-$^{13}$C]acetate.

FIGS. 5A, 5B, and 5C show plots of total glutamate C2 and C4 intensity versus time collected from a heart perfused with 0.5 mM [1,2-$^{13}$C]acetate, 1 mM [3-$^{13}$C]lactate, and 10 mM unenriched glucose.

DETAILED DESCRIPTION OF THE PREFERRED EMBODIMENTS

The invention is a rapid, efficient $^{13}$C NMR method of measuring substrate utilization under substantially in vivo conditions in virtually any tissue which has an active citric acid cycle. The method works with any substrate that provides acetyl CoA for the citric acid cycle. In practice, one or more $^{13}$C-labeled substrates is administered and a single NMR measurement is made within a short period after administration without the need to achieve metabolic or isotopic steady state. Measurements are made on $^{13}$C multiplet resonances shortly after administration of one or more labeled substrates. The spectrum is analyzed using a homonuclear decoupling procedure that collapses multiple lines to a baseline triplet. This allows measurement of substrate utilization in vivo, as the inventors have demonstrated with measurements made on intact, beating hearts.

The new methods do not require specialized apparatus for performing labeling procedures. Studies with labeled substrates may be performed under a wide variety of conditions. In vitro studies by the inventors have shown that the methods apply to numerous cells and tissues. Application to virtually any tissue or cell by a practitioner with basic skills in the art is possible once the conditions and analyses as herein described are known.

An advantage of the present invention is that NMR measurements may be made prior to attainment of a metabolic or isotopic steady state. More importantly, by applying the decoupling methods developed by the inventors, substrate utilization information taken from measurements in intact, metabolizing tissue is now possible. Thus the methods of the present invention are applicable to in vivo determinations of substrate utilization. Rapid determination of metabolic aberrations and abnormalities is now possible; for example, changes subsequent to injury or in diseases.

A typical and important use of the method is to assess heart muscle metabolism. Heart metabolism has been studied in detail so that there is a large amount of information on normal and abnormal heart function. Heart muscle utilizes large amounts of substrate to supply its constant need for energy production.

Significant metabolic changes occur after a heart attack. Certain drugs interfere with fatty acid oxidation which may have a beneficial effect on recovery. Whether or not such a drug would be effective in vivo depends on suitable models and methods for measuring substrate selection in the healthy versus the damaged heart. Classically, the majority of methods to determine such differences have concentrated on the measurement of substrate concentrations in the blood and/or blood flow or imaging during the first few minutes after damage to the heart occurs, typically employing radioactive tracers. Quantitation of substrate selection requires a steady state condition; therefore, measurements immediately after damage has occurred are not performed. Moreover, for in vivo human situations, the use of radioactive materials is clearly not in the best interest of the patient, being inconvenient and may in fact in some cases be dangerous.

Other similar methods require prolonged administration of labeled compounds. For example, infusion of $^{13}C$ labeled fatty acids alone requires at least 30 min. However, even this study would provide little indication of the effect of a given drug on a heart attack because several measurements would have to be taken subsequent to the infusion. In direct contrast, the method of the present invention employs only a single spectrum after infusion, thereby requiring a minimal amount of time to make a measurement in vivo; such measurement being made over a relatively short period while the subject is positioned in an NMR spectrometer. Except for the procedures involved in obtaining a spectrum, little training in working up the data is necessary, as data analysis is straightforward. Thus an obvious advantage of the new method is that a spectrum may be taken shortly after perfusion of labeled compounds. There is no assumption of steady state. Infusion for prolonged periods is not required and meaningful results on, i.e. , fatty acid oxidation may be obtained. On the other hand, traditional approaches require continuous infusion, information comes from the rate of $^{13}C$ enrichment in product molecules, and spectral data must be acquired from several spectra acquired periodically, typically every 5 to 10 minutes. This would be the case for example in the methods described in Behar, et al (1986) which employed time dependent measurements.

In typical practice of the invention, a suitable $^{13}C$ labeled substrate is administered to a subject, NMR measurement is taken and the NMR spectrum analyzed for isotopomer enrichment. These fractional enrichments, the $F_{cx}$ variables, can be monitored at any time during isotopic equilibration and during changes in intermediate pool sizes from the glutamate C4 multiplet areas plus the C4/C3 ratio from a single $^{13}C$ spectrum. The equations which describe these relationships are:

$$C4D34*(C4/C3)=F_{c2} \quad (1)$$

$$C4Q*(C4/C3)=F_{c3} \quad (2)$$

C4D34 is the area of the doublet ($J_{34}$=34 Hz) representing those glutamate isotopomers with an enriched $^{13}C$ at both C3 and C4 but not at C5 while C4Q is the area of the doublet of doublets or quartet (combination of $J_{34}$=34 Hz and $J_{45=52}$ Hz) representing those isotopomers with $^{13}C$ at C3, C4 and C5. Both areas are reported as a fraction of the total C4 resonance area (combined areas of all multiplets=1, by definition). $F_{c2}$ is the fraction of acetyl-CoA derived from substrates which yield [2-$^{13}C$]acetyl-CoA and $F_{c3}$ is the fraction of acetyl-CoA derived from substrates which yield [1,2-$^{13}C$]acetyl-CoA. Thus, if one made available to tissue a mixture of substrates which could only yield [2-$^{13}C$]acetyl-CoA and [1,2-$^{13}C$]acetyl-CoA, $F_{c2}$ and $F_{c3}$ may be obtained directly from the glutamate C4D34 and C4Q multiplet contributions, providing these multiplets are well resolved. The unlabeled substrate contribution to acetyl-CoA, $F_{c0}$, may either be determined by difference ($F_{c0}$=1–$F_{c2}$–$F_{c3}$) or by measurement of the glutamate C3S' resonance area (actually, the sum of C3S+C3D23) during [$^{13}C$]homonuclear decoupling of glutamate C2. Note that the above parameters only provide a measure of relative flux of various substrates into through the acetyl-CoA pool which enters the citric acid cycle. Absolute flux of various substrates through this oxidative pathway could be derived from these parameters only if total citric acid cycle flux was known from $O_2$ consumption measurements or from other NMR measurements as described above.

The above relationships are independent of changing pool sizes, anaplerosis, and alterations in isotopomer composition of TCA cycle intermediates because of the unique relationship between acetyl carbons of acetyl-CoA and glutamate C4 and C5. Since acetyl-CoA condenses with oxaloacetate to tom citrate on each turn of the citric acid cycle and citrate carbons C4 and C5 are isotopically equivalent to glutamate C4 and C5, respectively, the $^{13}C$ isotopomer population of the acetyl-CoA pool feeding the cycle is reported by the $^{13}C$ spectrum of glutamate C4 and C5 averaged over the period of time necessary to collect the spectrum. If the size of one or more citric acid cycle intermediate pools is changing or if anaplerotic flux of other molecules (either labeled or unlabeled) through a cycle intermediate is changing during this measurement, this would be reflected as time dependent changes in the total areas of glutamate C2, C3 and C4 and in some of the multiplet components of those resonances but not in relative multiplet areas of C4D34 versus C4Q. These depend only upon relative entry of singly versus doubly $^{13}C$-enriched acetyl groups into the citric acid cycle on each turn and hence are independent of pool sizes, anaplerosis, or other steady-state requirements. The only requirement is that the enough $^{13}C$ must have entered the glutamate pool via acetyl-CoA→citrate→isocitrate→α-ketoglutarate→ glutamate to allow detection by $^{13}C$ MRS.

Based upon numerous isolated, perfused heart experiments, a typical $^{13}C$ linewidth, a protonated glutamate carbon resonance in vivo would be no worse than about 12–15 Hz. This makes feasible a resolution of the glutamate C2 and C4 three-line multiplets in a (C3)homonuclear decoupled spectrum, thereby allowing a continuous measurement of substrate utilization for any mixture of $^{13}C$-enriched substrates of interest. In cases where triplet resonances are not adequately resolved in vivo, homonuclear decoupling techniques have been applied to separate out the singlet and doublet contributions to each three-line multiplet. Hence, significant information about intermediary metabolism in vivo by $^{13}C$ magnetic resonance without steady-state assumptions is now possible. Since the technique demonstrated here is easy to implement on any spectrometer, it is useful for monitoring temporal changes in substrate selection which may accompany altered metabolic events resulting from ischemia or administration of drugs.

The invention therefore may be employed for any tissue or cell measurements in which steady-state metabolic or isotopic conditions have not been attained. The method determines the sources of acetyl-CoA and assumes only that acetyl-CoA has become enriched in carbon from a carbon-labeled substrate.

It is an assumption of the method that oxaloacetate has become enriched in $^{13}C$. The only oxaloacetate carbon position relevant to the nonsteady-state analysis is the carbonyl carbon, C2, since this carbon becomes C3 of glutamate after ½ turn of the citric acid cycle. C4 and C3 of oxaloacetate become, respectively, C1 and C2 of glutamate and are not involved in this analysis. C1 of oxaloacetate is lost as $CO_2$ at the isocitrate dehydrogenase step. Because relative enrichments in the acetyl-CoA pool are being examined, the absolute enrichment in the C2 of oxaloacetate need not be known.

The theory of this method will be presented for moderately complex conditions which produce three acetyl-CoA isotopomers, for example, the use of [U-$^{13}C$]glucose and [3-$^{13}C$]lactate. More complex conditions are described below. The chance that an oxaloacetate molecule labeled in the 2 carbon will condense with a given acetyl-CoA isotopomer equals the relative concentration of that isotopomer in the acetyl-CoA pool. Three different acetyl-CoA isotopomers may occur under these illustrative conditions: unlabeled acetyl-CoA from unlabeled sources, [2-$^{13}C$]acetyl-CoA from lactate, and [1,2-$^{13}C$]acetyl-CoA from glucose. Their relative concentrations are defined as $F_{c0}$, $F_{c2}$ and $F_{c3}$, respectively. Although glutamate has 32 possible isotopomers, only 24 may occur under these conditions (since there is no pathway for generation of [1-$^{13}C$]acetyl-CoA). Variables which indicate the relative concentrations of glutamate isotopomers are:

$X_1$=[[1,2,3,4,5-$^{12}C$]glutamate]/[glutamate]
$X_2$=[[1-$^{13}C$]glutamate]/[glutamate]
$X_3$=[[2-$^{13}C$]glutamate]/[glutamate]
$X_4$=[[1,2-$^{13}C$]glutamate]/[glutamate]
$X_5$=[[3-$^{13}C$]glutamate]/[glutamate]
$X_6$=[[1,3-$^{13}C$]glutamate]/[glutamate]
$X_7$=[[2,3-$^{13}C$]glutamate]/[glutamate]
$X_8$=[[1,2,3-$^{13}C$]glutamate]/[glutamate]

Similarly, $X_9$–$X_{16}$ are identical to the first group, except that carbon 4 (but not carbon 5) is enriched. Enrichment in carbon 5 but not carbon 4 is represented by $X_{17}$–$X_{24}$, which in this case are 0. Finally, $X_{25}$–$X_{32}$ refer to the same pattern of labeling in carbons 1, 2 and 3, plus labeling in both carbons 4 and 5. By definition, $F_{c0}+F_{c2}+F_{c3}=1$, and $X_1+X_2+ \ldots +X_{32}=1$. Six groups of glutamate isotopomers may be defined as:

| | |
|---|---|
| $W_1 = X_1 + X_2 + X_3 + X_4$ | (not labeled in C3, C4 or C5) |
| $W_2 = X_5 + X_6 + X_7 + X_8$ | (labeled in C3 but not C4 or C5) |
| $W_3 = X_9 + X_{10} + X_{11} + X_{12}$ | (no lableled in C3 or C5, labeled in C4) |
| $W_4 = X_{13} + X_{14} + X_{15} + X_{16}$ | (labeled in C3 and C4, not labeled in C5) |
| $W_5 = X_{25} + X_{26} + X_{27} + X_{28}$ | (not labeled in C3, labeled in C4 and C5) |
| $W_6 = X_{29} + X_{30} + X_{31} + X_{32}$ | (labeled in C3, C4 and C5) |

The area of the 4 carbon resonance relative to the 3 carbon resonance is defined as $C4/C3=(W_3+W_4+W_5+W_6)/(W_2+W_4+W_6)$. The area of the components of the 4 carbon multiplet are defined relative to the total area of the resonance (Chance, et al., 1983): singlet, C4S; doublet due to $J_{34}$, $C4D34=W_4/(W_3+W_4+W_5+W_6)$; doublet due to J45, C4D45; doublet of doublets (quartet), $C4Q=W_6/(W_3+W_4+W_5+W_6)$.

$F_{c0}$, $F_{c2}$ and $F_{c3}$ are quantitatively related to $W_2$, $W_4$, and $W_6$, respectively. The chance that an oxaloacetate molecule labeled in C2 will condense with unlabeled acetyl-CoA equals $F_{c0}$. Therefore, $F_{c0}/(F_{c0}+F_{c2}+F_{c3})=W_2/(W_2+W_4+W_6)$. Similar relations may be derived for $F_{c2}$ and $F_{c3}$. By combining these relationships, one obtains quite simply, $$(C4D34)(C4/C3)=W_4/(W_2+W_4+W_6)=F_{c0}/(F_{c0}+F_{c2}+F_{c3})=F_{c2} \quad \text{Equation [1]}$$

$$(C4Q)(C4/C3)=W_6/(W_2+W_4+W_6)=F_{c3}/(F_{c0}=F_{c2}+F_{c3})=F_{c3} \quad \text{Equation [2]}$$

Therefore, by measuring two C4 multiplet components and the C4/C3 ratio, one can obtain values for $F_{c2}$, $F_{c3}$ and by difference, $F_{c0}$, under any nonsteady-state circumstances.

In practice, $B_0$ field homogeneity may not be adequate to resolve $^{13}C$-$^{13}C$ coupling, however, under these circumstances, special pulse sequences may be employed. A J modulated spin echo may be used to select the phase of each multiplet in a resonance (LeCocq and Lallemand, 1981; Patt and Shoolery, 1982) since the evolution of a spin system under the influence of scalar coupling is not altered by $B_0$ inhomogeneity. The pulse sequence 90°-τ-180°-τ acquire (where τ=½J) was used to create a 180° phase difference between the doublet ($J_{34}$=34 Hz) and the other lines in the C3 and C4 resonance under conditions producing well resolved or poorly resolved resonances. Two fully relaxed spectra may be accumulated (preferably over the same time period in separate regions of computer memory), using a single pulse and a second using the spin-echo sequence. The C4/C3 ratio is obtained from the first spectrum 7A and C4D34 is obtained from the difference between the two spectra, (C4D34=(A−B)/2A=0.5−B/2A, where A is the area of the C4 resonance after a standard scan and B is the area with a spin echo.)

This analysis may be extended to more complex substrate combinations and metabolic conditions. [1-$^{13}C$]acetyl-CoA may be generated from a labeled compound provided to the tissue such as [2-$^{13}C$]lactate, or by $^{13}C$ flowing from oxaloacetate to phosphoenolpyruvate, pyruvate, and ultimately acetyl-CoA. Under either circumstance the resulting glutamate may become enriched in C5 but not C4. This analysis (equations 1 and 2) would remain valid, but the fraction of acetyl-CoA which is unlabeled ($F_{c0}$) could not be distinguished from the fraction of acetyl-CoA enriched in C1. The ratio $F_{c1}/F_{c3}$ may be determined directly from the multiplets in the $^{13}C$ NMR resonance of the C5 of glutamate: $F_{c1}/F_{c3}$=C5S/C5D, where C5S and C5D refer to the areas of the singlet and doublet. However, appropriate experimental conditions or corrections must be used to quantify the $^{13}C$-enrichment in glutamate C5 because of the effects of $^{13}C$-$^{13}C$ dipolar interaction on $T_1$ (London, 1988; Walker, et al., 1982; Chance, et al., 1983). Hence, the relative concentrations of all 4 acetyl-CoA isotopomers may be determined in a single experiment.

The following examples are intended to illustrate specific embodiments of the present invention, not to exhaustively describe all possible embodiments. Those skilled in this field will recognize that modifications could be made to the disclosed methods and that other applications would remain within the scope of the present invention.

Methods and materials employed in the practice of the invention are set forth below.

Heart Perfusions. Male Sprague-Dawley rats weighing 300–350 g were anesthetized in an ether atmosphere and hearts were rapidly excised and placed in 4° C. arrest medium. Hearts were perfused using standard Langendorff methods at a pressure of 70 cm of $H_2O$ by recirculating 125 ml of Krebs-Henseleit buffer. Typical coronary flow rates were 15–18 ml/min. A modified Krebs-Henseleit perfusate containing 119.2 mM NaCl, 4.7 mM CK1, 1.45 mM $CaCl_2$, 1.2 mM $MgSO_4$, 25 mM $NaHCO_3$, and 10 mM glucose was bubbled with 95% $O_2$/5% $CO_2$. Hearts were initially perfused with 10 mM glucose as the only exogenous substrate and $^{13}C$ enriched substrates were added to the 125 ml perfusion chamber from a standardized stock solution. All freeze-clamped hearts were extracted with cold perchloric acid, neutralized with KOH, freeze-dried, and dissolved in 0.5 ml of $D_2O$ for NMR analyses. Sodium [3-$^{13}C$]lactate (99%, Isotec) and sodium [1,2-$^{13}C$]acetate (99%, MSD Isotopes) were used without further purification.

NMR Methods. Proton-decoupled $^{13}C$ spectra were obtained at 125.7 MHz on a GN-500 spectrometer equipped with a second broad-band decoupling channel. Intact heart spectra were collected in a 18 mm thin-walled NMR tube (Wilmad) with the heart bathed in perfusate, as previously described (Schwaiger, et al., 1985). The temperature of the heart was maintained at 37° C. by control of the circulation perfusate temperature and by temperature control of the air surrounding the 18 mm NMR tube in the magnet using the GE VT assessory. Typically, spectra were signal-averaged over periods ranging from 5 to 20 minutes using a 45° carbon pulse, a sweep width of ±14,000 Hz, 16K data points, and a 1 s delay between pulses. Efficient proton decoupling was achieved using WALTZ decoupling at two power levels, low during the 1 s delay and high during the short acquisition period. Shimming was performed on the $^{13}C$ observe coil after tuning to $^{23}Na$ (132 MHz). A typical $^{23}Na$ line width on an intact heart sample was about 18–20 Hz. Spectra of heart extracts were obtained in a 5 mm tube using a 45° carbon pulse, 16K data points over ±14,000 Hz, and a 6 s delay between pulses. Broad band proton decoupling was achieved using WALTZ decoupling at two power levels (BILEV) and the temperature was maintained at 25° C. All spectra were zero-filled to 32K points before Fourier transformation. Homonuclear $^{13}C$ decoupling was achieved using single frequency decoupling generated by the spectrometer's F3 channel; the output of this decoupler was passed through a series of cross-diodes to filter out noise from the broad-band amplifier and connected to the observe coil through a directional coupler (supplied by GE).

The relative areas of the multiplet components in each glutamate resonance were measured and compared using two deconvolution programs, GEMCAP (supplied with the GE software) and NMR-286 (SoftPulse Software, Guelph, Ontario, Canada). The first program (GEMCAP) is operator dependent, requiring manual fitting of calculated versus observed multiplets while the second (NMR-286) performs a least square fitting of the multiplet areas, requiring only identification of the number of resonances within each resonance. Both fitting procedures gave identical multiplet areas to within ±2%.

Figure 1A:
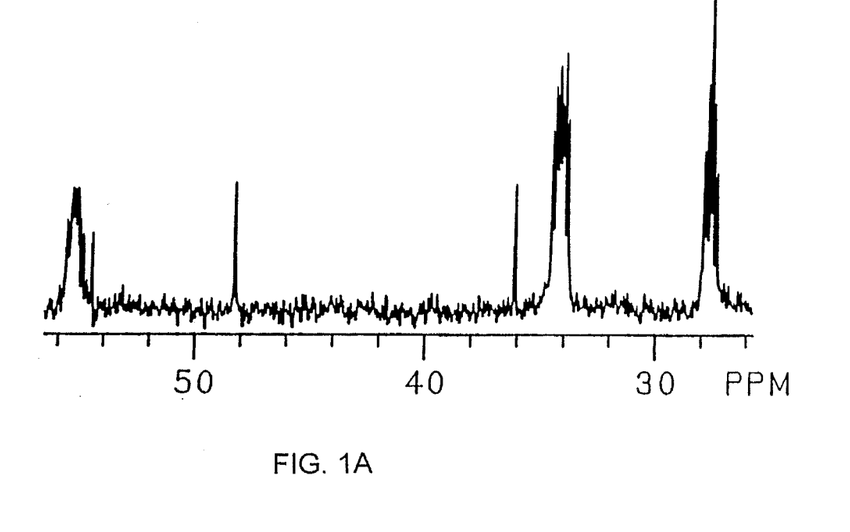
FIGS. 1A and 1B show a $^{13}$C MRS spectra of the extract of a rat heart perfused with 1 mM [3-$^{13}$C]lactate and 0.25 mM[1,2-$^{13}$C]acetate.
Figure 1B:
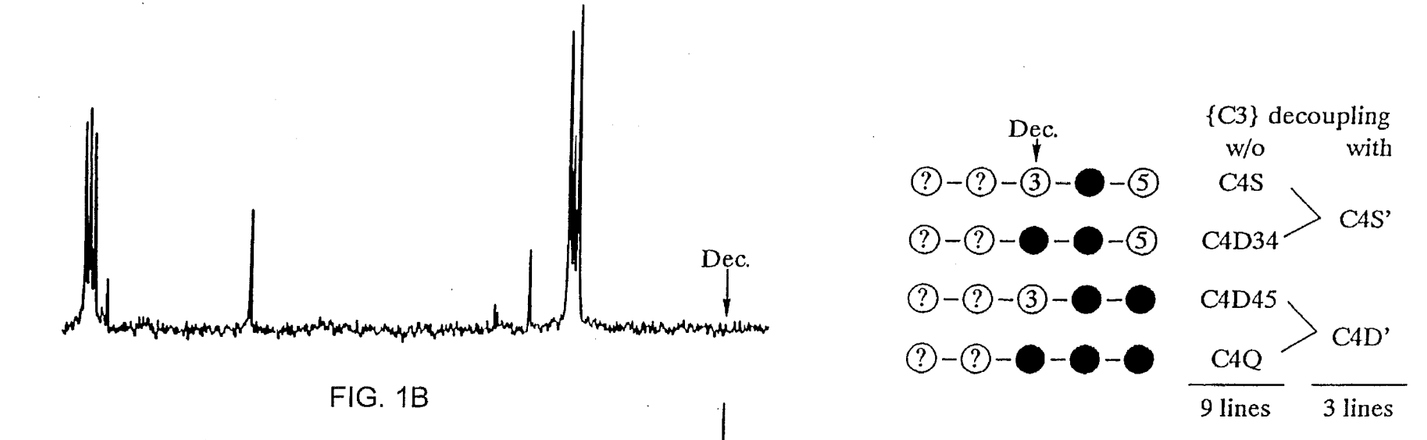

Extract Spectra: The $^{13}C$ spectrum of an extract of a heart perfused to steady-state with a mixture of 10 mM unenriched glucose, 1 mM [3-$^{13}C$]lactate and 0.25 mM [1,2-$^{13}C$] acetate is shown in FIG. 1A. This substrate mixture provides mix of acetyl-CoA isotopomers to the heart; unenriched acetyl-CoA (as measured by $F_{c0}$), methyl-enriched acetyl-CoA (as measured by $F_{c2}$), and doubly enriched acetyl-CoA (as measured by $F_{c3}$). Although there is substantial metabolic information in this glutamate spectrum (Malloy, et al., 1990), each resonance appears as a 5–9 line $^{13}C$ multiplet and these would not be sufficiently resolved in an in vivo spectrum to allow an isotopomer analysis. However, upon selective homonuclear decoupling of glutamate C3 (FIG. 1B), the nine-line C2 and C4 resonances collapse into three lines, with a 52 Hz separation between the outer lines (representing $J_{1,2}$ and $J_{4,5}$, respectively). Simple inspection of the diagram to the right of these spectra illustrates that the singlet in the [C3]homonuclear decoupled spectrum (designated as C4S' to distinguish it from the C4S in the non-decoupled spectrum) reports the fraction of methyl-enriched acetyl-CoA ($F_{c2}$) derived from [3-$^{13}C$]lactate while C4D' reports the fraction of double-enriched acetyl-CoA ($F_{c3}$) derived from [1,2-$^{13}C$]acetate. Thus, the ratio of lactate/acetate utilized by this heart is directly reported by the C4S'/C4D' ratio, equal to 0.22/0.78 or 0.28 in this spectrum.

The spectral simplification provided by [C3]homonuclear decoupling does not preclude a more complete steady-state analysis of the decoupled spectrum. A summation of the multiplet equations for C4S and C4D34 and for C2S and C2D23 yields new steady-state equations representing C4S', C2S', and y in the [C3]homonuclear decoupled spectrum.

$$(C4/C2)=2y+1 \quad (3)$$

$$C4S'=F_{c2}/(F_{c2}+F_{c3}) \quad (4)$$

$$C2S'=[F_{c2}(2y+1)/(F_{c2}+F_{c3})(2y+2)]+[(1-F_{c2}-F_{c3}+y)/2(y+1)^2] \quad (5)$$

Substitution of equation 3 into 5 yields two equations containing two unknowns. A quick check of the validity of these equations was performed as follows. First, the computer program, tcaSIM, was used to generate multiplet areas of glutamate C2, C3 and C4 at steady-state for various input values of $F_{c2}$, $F_{c3}$ and y. Values for C4S and C4D34 were then summed to give C4S' and C2S and C2D23 were summed to give C2S'. Equations 3–5 were then solved using these data, giving the exact expected values of $F_{c2}$, $F_{c3}$, and y. This confirmed the validity of equations 3–5.

Figure 2:
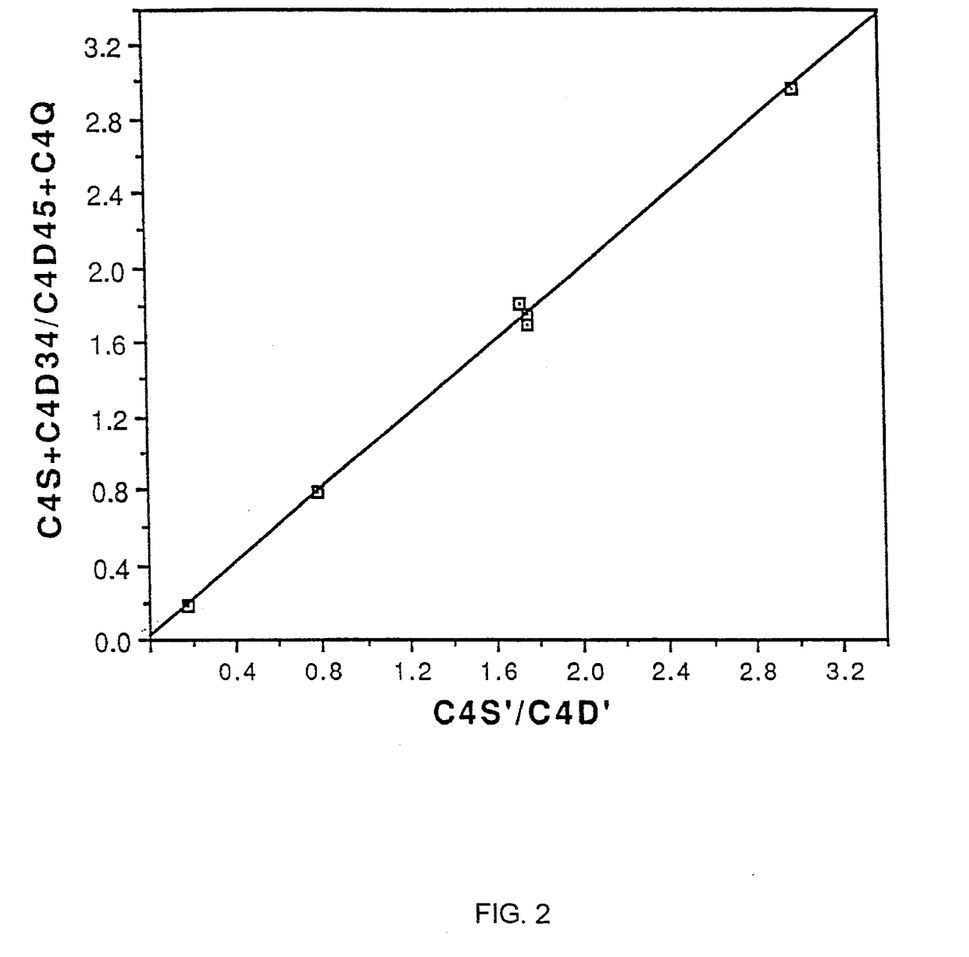
FIG. 2 shows a comparison of glutamate multiplet areas obtained with and without homonuclear decoupling of glutamate C3. The plot shows the ratio, (C4S+C4D34)/(C4D45+C4Q), obtained from high resolution spectra of six different heart extracts versus the ratio, C4S'/C4D', obtained from (C3)homonuclear decoupled spectra of those same extracts.

There may be unanticipated consequences of $^{13}C$ decoupling for quantitation of multiplet areas. Therefore, a series of heart extract spectra were run with and without [C3] homonuclear decoupling. If decoupling of glutamate C3 was efficient and technical difficulties such as power leakage are avoided, the expected experimental values of C4S +C4D34 and C4D45+C4Q in the coupled spectrum should equal C4S' and C4D', respectively, in the (C3)homonuclear decoupled spectrum. A plot of these multiplet area comparisons for six different heart extracts covering a wide range of metabolic parameters is shown in FIG. 2. This plot shows near perfect agreement (slope=1) between the multiplet resonance areas in the coupled versus the decoupled spectra. Hence, derivation of metabolic parameters from spectra of heart extracts (where resolution of the multiplets and signal-to-noise is not limited) using either the complete steady-state analysis (Malloy, et al., 1988; Malloy, et al., 1990) or the equations presented above give identical results.

In those instances where signal-to-noise is limited due to sample size or time constraints, homonuclear decoupling appears to be advantageous because there is also a gain in signal-to-noise resulting from collapse of the 5 to 9 line multiplets into 3 line multiplets. The actual gain in signal-to-noise depends upon the relative sizes of C4S versus C4D34 and C4D45 versus C4Q in the coupled spectrum.

A summary of theoretical versus actual experimental gains in signal-to-noise for four different extract spectra is given in Table 2. These data show that the gain in signal-to-noise resulting from homonuclear decoupling of glutamate C3 can be substantial (≈130%) when the population of glutamate isotopomers which contribute to either C4D34 or C4Q is high.

EXAMPLE 1

This method illustrates analysis of a $^{13}C$ spectrum of an intact, beating rat heart perfused with [1,2-$^{13}C$]acetate.

Figure 3A:
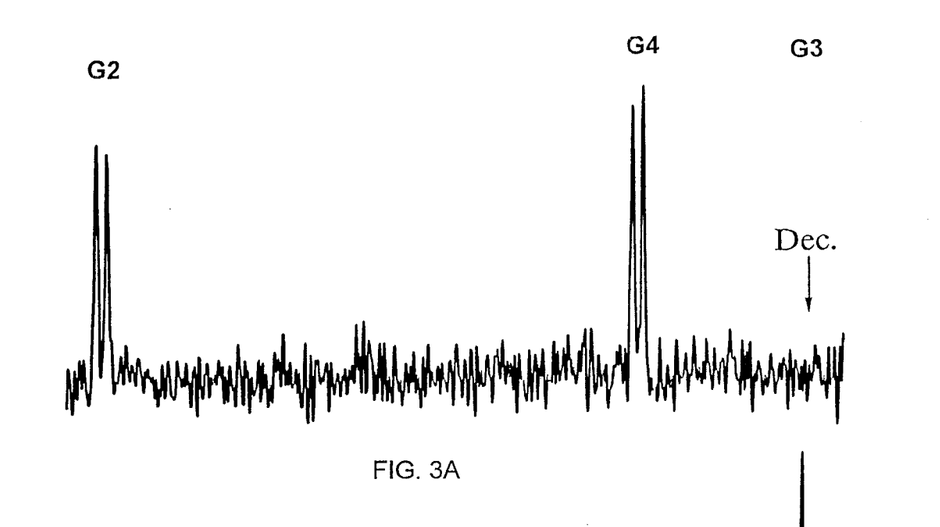
FIG. 3A is a (C3)homonuclear decoupled spectrum showing how C2 and C4 collapse into well resolved doublets.
Figure 3B:
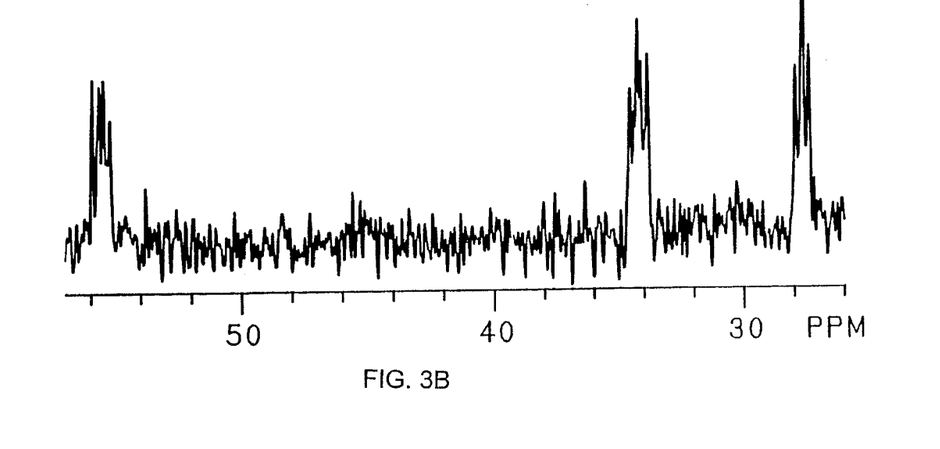
FIG. 3B is normal $^{13}$C spectrum illustrating the complex multiplets in the glutamate C2, C4 and C3 resonances.

Intact heart spectra: A typical $^{13}C$ spectrum of a heart perfused with 3 mM [1,2-$^{13}C$]acetate is shown in FIG. 3B. The six-line C4 resonance resulting from overlap of the C4D45 and C4Q multiplets (Malloy, et al., 1989) is not fully resolved and the nine-line C2 resonance shows even less detail. However, homonuclear decoupling of glutamate C3 simplifies both the C2 and C4 resonances into baseline resolved doublets with the expected 52 Hz coupling constants (FIG. 3A). The spectra in FIGS. 4A and 4B show this same heart after addition of ~1.5 mM [2-$^{13}C$]acetate.

The C4 resonance in the absence of (C3)homonuclear decoupling contains four multiplets (9 lines), making resolution even more problematical. The decoupled spectrum (top) shows the expected three lines, representing C4S' and C4D'. The individual areas of these multiplets were easily measured, giving a C4S'/C4D'=0.45. This indicated that the relative utilization of [2-$^{13}C$]acetate versus [1,2-$^{13}C$]acetate was about 1:2, as expected for the relative concentrations of these two substrates in the perfusate. When values for C2S' and the total C4/C2 ratio were included with the information from C4S', absolute values of $F_{c2}=0.26$, $F_{c3}=0.57$, and y=0.18 were derived from equations 3–5, values well within the normal range expected for these parameters in acetate perfused hearts (Malloy, et al., 1988; Malloy, et at., 1990).

Figure 5B:
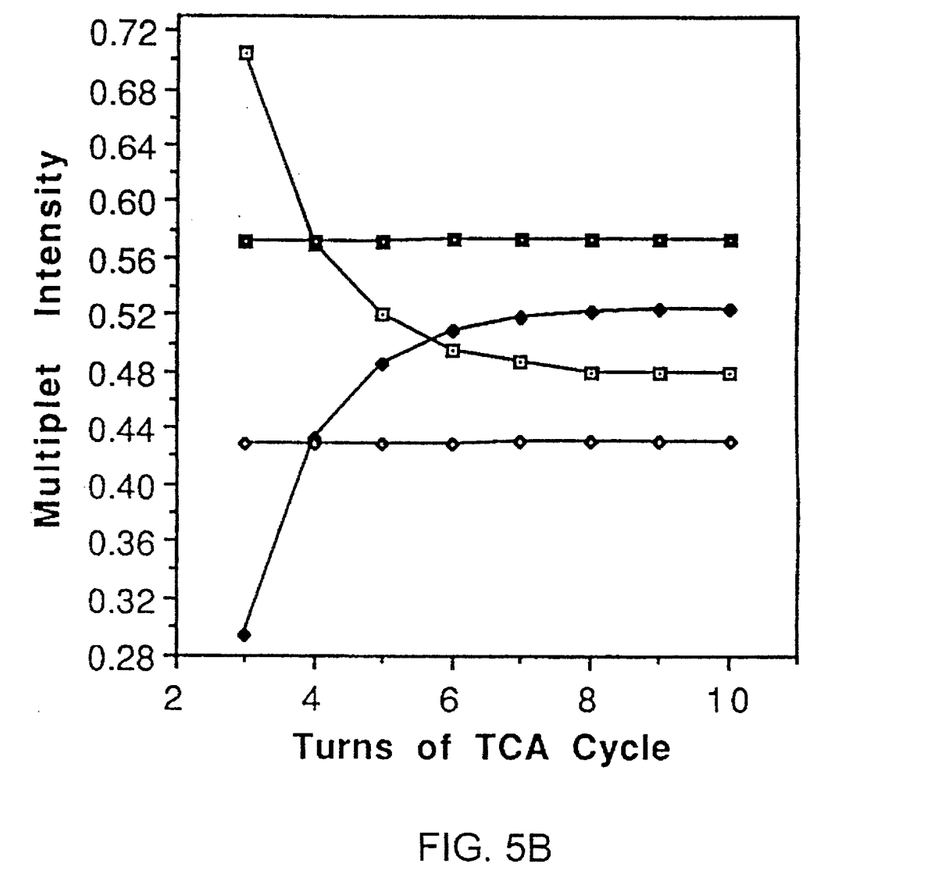
FIG. 5B shows calculated values of C4S' (■), C4D' (◊), C2S' (□) and C2D' (♦) as a function of turns through the citric acid cycle pools (upper right).

A series of hearts presented with a mixture of competing substrates, 1 mM [1,2-$^{13}C$]acetate and 3 mM [3-$^{13}C$]lactate, were examined using the homonuclear decoupling technique outlined above as a function of time after addition of the $^{13}C$ enriched materials to the perfusion chamber. A plot of the total intensity of the C4 and C2 resonances (fractional $^{13}C$ enrichment at each glutamate carbon position) averaged over 3 minute intervals is shown in FIG. 5A. The differential times for half-maximal enrichment of C4 versus C2 provides a measure of citric acid cycle flux (Weiss, et al., 1992, 1993). Shown in FIG. 5B are the time dependent changes in C2S', C2D', C4S' and C4D', calculated using tcaSIM. This shows that C4S' and C4D' are time-independent parameters while C2S' and C2D' evolve with time. This indicates that temporal changes in C2S' and C2D' could be used to monitor citric acid cycle flux.

Figure 5C:
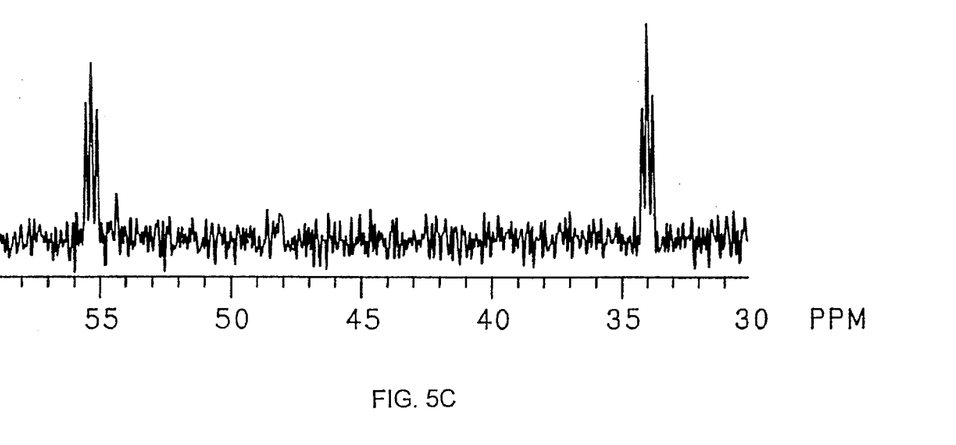
FIG. 5C is a tracing showing the (C3)homonuclear decoupled spectrum of this heart of steady-state. This spectrum represents the average of 800 scans collected over 16 minutes.

FIG. 5C shows a [C3]homonuclear decoupled spectrum of this heart after reaching steady-state levels of $^{13}C$ enrichment in both C2 and C4. Analysis of spectra such as this using equations 3–5 gave the following results (n=4): $F_{c2}=0.25\pm0.06$, $F_{c3}=0.31\pm0.04$, and y~0. This indicates that [1,2-$^{13}C$]acetate contributed 31%, [3-$^{13}C$]lactate contributed 25%, and unenriched endogenous sources contributed 44% of the total acetyl-CoA entering the citric acid cycle in these hearts, values that are identical to those measured previously (Sherry, et al., 1992) from high resolution $^{13}C$ NMR spectra of extracts using both steady-state and non-steady-state analyses.

TABLE 2

Theoretical versus experimental gain in glutamate C4 resonance signal-to-noise resulting from homonuclear decoupling of the C3 resonance in four different spectra of heart extracts.

| C4S | C4S' Theoretical Gain in | C4S' Experimental Gain in | C4D45 | C4D' Theoretical | C4D' Experimental Gain in |
|---|---|---|---|---|---|
| C4D34 | S/N | S/N | C4Q | Gain in S/N | S/N |
| 2.94 | 34% | 37% | 3.04 | 17% | 19% |
| 1.36 | 74% | 80% | 1.14 | 44% | 49% |
| 1.05 | 95% | 89% | 0.99 | 50% | 46% |
| 0.90 | 110% | 100% | 0.37 | 137% | 129% |

While the methods and compositions of this invention have been described in terms of preferred embodiments, it will be apparent to those of skill in the art that variations may be applied to the methods or compositions and in the steps or sequence of steps of the methods described herein without departing from the concept, spirit and scope of the invention. More specifically, it will be apparent that the methods apply to any metabolizing tissue or cell in which a labeled substrate can be measured, whether by $^{13}C$ NMR or by other methods of determination and different labels. All such similar substitutes apparent to those skilled in the art are deemed to be within the spirit, scope and concept of the invention as defined by the appended claims.

REFERENCES

The references listed below are incorporated herein by reference to the extent they supplement, explain, provide a background for or teach methodology, techniques and/or compositions employed herein.

Avison et al., "Detection of human muscle glycogen by natural abundance $^{13}C$ NMR," *Proc. Natl. Acad. Sci. USA*, 85:1634–1636 (1988).

Behar, K. L., Petroff, O. A. C., Prichard, J. W., Alger, J. R. and Shulman, R. G., "Detection of Metabolites in Brain by $^{13}C$ NMR Spectroscopy following Administration of [1-$^{13}C$]-glucose" *Magn. Reson. Med.*, 3:911–920(1986).

Bottomley et al., "Proton-decoupled, overhauser-enhanced, spatially localized carbon-13 spectroscopy in humans," *Magn. Reson. Med.*, 12:348–363 (1989).

Brown, M., Marshall, D. R., Sobel, B. E. and Bergmann, S. R. Circulation 76, 687–696 (1987).

Chance et al. "Mathematical analysis of isotope labeling in the citric acid cycle with applications to $^{13}C$ NMR in perfused rat hearts," *J. Biol. Chem.*, 258:13785–13794 (1983).

Chatzidakis, C. and Otto, D. A. Lipids 22, 620–626 (1987).

Cohen, S. M. J. Biol. Chem. 258, 14294–14308 (1983).

Heershap et al., "Broadband proton decoupled natural abundance $^{13}C$ NMR spectroscopy of humans at 1.5T". *NMR Biomed.*, 2:124–132 (1990).

Jue et al., "Natural abundance $^{13}C$ NMR spectrum of glycogen in humans," *Magn. Reson. Med.*, 5:377–379 (1987).

Kornberg, H. L. Essays Biochem. 2, 1–31 (1966).

LeCocq and Lallemand, "Precise carbon-13 NMR multiplicity determination," *J. Chem. Soc. Chem. Commun.*, 150–152 (1981).

LeCocq, C. and Lallemand. J.-Y. J. Chem. Soc. Chem. Commun. 15–152 (1981).

Lerch, R. A., Ambos, H. D., Bergmann, S. R., Welch, M. J., Ter-Pogossian, M. M. and Sobel, B. E. Circulation 64, 689–699 (1981).

Liedke, J., DeMaison, L., Eggleston, A. M., Cohen, L. M. and Nellis, S. H. Circulation Research 62, 535–542 (1988).

London, R. E. Progress in NMR Spectroscopy 20, 337–383 (1988).

Magnusson et al. "Increased rate of gluconeogenesis in type II diabetes mellitus: a $^{13}$C NMR study," *J. Clin. Invest.*, 90:1323–1327 (1992).

Malloy et al. "Evaluation of carbon flux and substrate selection through alternate pathways involving the citric acid cycle of the heart by $^{13}$C NMR spectroscopy," *J. Biol. Chem.*, 263:6964–6971 (1988).

Malloy et al. "Analysis of the TCA cycle of the heart using $^{13}$C isotope isomers," *Am. J. Physiol.*, 259:H987–H995 (1990A).

Malloy et al. "Contribution of exogenous substrates to acetyl-coenzyme A: measurement by $^{13}$C NMR under nonsteady-state conditions," *Biochemistry*, 29:6756–6761 (1990B).

Malloy, C. R. in Structural and Organizational Aspects of Metabolic Regulation, Alan R. Liss, Inc. (1990C), pp. 363–374.

Malloy, C. R., Sherry, A. D., and Jeffrey, F. M. H. J. Biol. Chem. 263, 6964–6971 (1988).

Mickel, D. A. G., del Nido, P. J., Wilson, G. J., Harding, R. D., and Romaschin, A. D. Cardiovas. Res. 20, 256–263 (1986).

Moreland, C. G., and Carroll, F. I. J. Magn. Res. 15, 596–599 (1974).

Myears, D. W., Sobel, B. E., and Bergmann, S. R. Am. J. Physiol. 253, H107–H114 (1987).

Neely, J. R., Denton, R. M., England, P. J., and Randle, P. J. Biochem. J. 128, 147–159 (1972).

Patt, S. L. and Shoolery, J. N. J. Magn. Res. 46, 487–495 (1982).

Patt and Shoolery, "Attached proton test for carbon-13 NMR," *J. Magn. Reson.*, 46:535–539 (1982).

Peuhkurinen, K. J. J. Mol. Cell. Cardiol. 16, 487–495 (1980).

Rothman et al. "Quantitation of hepatic glycogenolysis and gluconeogenesis in fasting humans by $^{13}$C NMR," *Science*, 254:573–576, (1991).

Schwaiger, M., Schelbert, H. R., Keen, R., Vinten-Johansen, J., Hansen, H., Selin, C., Barrio, J., Huang, S. C. and Phelps, M. E. J. Am. Coil. Cardiol. 6, 311–320 (1985).

Sherry et al. "Alterations in substrate utilization in the reperfused myocardium: a direct analysis by $^{13}$C NMR," *Biochemistry*, 31:4833–4837 (1992).

Sherry, A. D., Malloy, C. R., Roby, R. E., Rajogopal, A. and Jeffrey, F. M. H. Biochem. J. 254, 593–598 (1988).

Shulman et al., "Quantitation of muscle glycogen synthesis in normal subjects and subjects with non-insulin-dependent diabetes by $^{13}$C NMR spectroscopy," *N. Eng. J. Med.*, 322:223–228 (1990).

Veerkamp, J. M., van Moerkerk, H. T. B., Glatz, J. F. C., Zuurveld, J. G. E. M., Jacobs, A. E. M., Wagenmakers, A. J. M. Biochem. Med. Metab. Biol. 35, 248–259 (1986).

Walker, T. E. and London, R. E. Appl. Environ. Microbiol. 53, 92–98 (1987).

Walker, T. E., Han, C. H., Kollman, V. H., London, R. E. and Matwiyoff, N. A. J. Biol. Chem. 257, 1189–1195 (1982).

Walsh, K. and Koshland, D. E., Jr., J. Biol. Chem., 9646–9654 (1984).

Weiss et al. "TCA cycle activity in postischemic rat hearts," *Circulation*, 87:270–282 (1993).

Weiss et al. "Indexing TCA cycle flux in intact hearts by $^{13}$C NMR," *Cir. Res.*, 70:392–408 (1992).

Williamson, J. R. and Krebs, H. A. Biochem. J. 80, 544–547 (1961).

Williamson, J. R. Biochem. J. 257, 1189–1195 (1962).

Wyns, W., Schwaiger, M., Huang, S.-C., Buxton, D. B., Hansen, H., Selin, C., Keen, R., Phelps, M. E., and Schelbert, H. R. Circ. Res. 65, 1787–1797 (1989).

What is claimed is:

1. A method of determining $^{13}$-C labeled substrate utilization in an intact, metabolizing tissue or cell, comprising:

introducing $^{13}$C-labeled substrate into a viable tissue or cell wherein said substrate is metabolized to acetyl Co-A;

measuring a $^{13}$C glutamate enrichment pattern;

selectively homonuclear decoupling C3 glutamate resonances to collapse glutamate C2 and C4 multiplets into a three line multiplet; and determining relative areas of collapsed resonances to obtain a measure of substrate utilization.

2. A method of determining $^{13}$-C labeled substrate utilization in an intact, metabolizing tissue or cell, comprising:

introducing $^{13}$C-labeled substrate into a viable tissue or cell wherein said substrate is metabolized to acetyl Co-A;

measuring a $^{13}$C glutamate enrichment pattern prior to attainment of metabolic or isotopic steady state;

selectively homonuclear decoupling C3 glutamate resonances to collapse glutamate C2 and C4 multiplets into a three line multiplet; and determining relative areas of collapsed resonances to obtain a measure of substrate utilization.

3. The method of claim 1 or claim 2 wherein the intact, metabolizing tissue is heart.

4. The method of claim 1 or claim 2 wherein the intact, metabolizing tissue is brain, liver, kidney, pancreas, lymphoid tissue, skeletal muscle or lung.

5. The method of claim 1 or claim 2 wherein the cell is a prokaryote or eukaryote.

6. The method of claim 1 or claim 2 wherein the cell is a yeast cell.

7. The method of claim 1 or claim 2 wherein the $^{13}$C labeled substrate is [3-$^{13}$C]lactate, [1,2-$^{13}$C]acetate or [3-$^{13}$C]lactate with [1,2-$^{13}$C]acetate.

8. The method of claim 1 or 2 wherein $^{13}$C spectra are signal averaged over a time period sufficient to provide a signal-to-noise ratio of about 3 to about 4.

9. The method of claim 1 or claim 2 wherein the homonuclear decoupling is obtained by WALTZ decoupling at two power levels, said power levels being low during a delay period and high during an acquisition period.

10. The method of claim 1 or claim 2 wherein the $^{13}$C-labeled substrate is a carboxylic acid.

11. The method of claim 10 wherein the carboxylic acid is acetate, propionate, butyrate, pentanoate, pentenoate, hexanoate, octanoate, decanoate, dodecanoate, tetradecanoate, hexadecanoate, octadecanoate, eicosanoate, palmitate, palmitoleate, oleate, linoleate, linolenate, stearate or arachidonate.

12. The method of claim 1 or claim 2 wherein the $^{13}$C-labeled compound is lactate, pyruvate, glucose, fructose, acetoacetate, β-hydroxybutyrate or ethanol.

* * * * *